United States Patent
Choi et al.

(10) Patent No.: US 9,545,189 B2
(45) Date of Patent: Jan. 17, 2017

(54) ENDOSCOPE USING DEPTH INFORMATION AND METHOD FOR DETECTING POLYP BASED ON ENDOSCOPE USING DEPTH INFORMATION

(71) Applicant: SAMSUNG ELECTRONICS CO., LTD., Suwon-si, Gyeonggi-do (KR)

(72) Inventors: Ouk Choi, Yongin-si (KR); Byong Min Kang, Yongin-si (KR); Do Kyoon Kim, Seongnam-si (KR); Chang Yeong Kim, Seoul (KR); Kee Chang Lee, Yongin-si (KR); Seung Kyu Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 461 days.

(21) Appl. No.: 14/045,277

(22) Filed: Oct. 3, 2013

(65) Prior Publication Data

US 2014/0187861 A1    Jul. 3, 2014

(30) Foreign Application Priority Data

Jan. 3, 2013    (KR) .......................... 10-2013-0000570

(51) Int. Cl.
| | |
|---|---|
| *A61B 1/00* | (2006.01) |
| *A61B 1/04* | (2006.01) |
| *A61B 1/06* | (2006.01) |
| *A61B 5/06* | (2006.01) |

(Continued)

(52) U.S. Cl.
CPC ....... *A61B 1/00193* (2013.01); *A61B 1/00009* (2013.01); *A61B 1/00177* (2013.01); *A61B 1/00181* (2013.01); *A61B 5/065* (2013.01); *A61B 5/1032* (2013.01); *A61B 1/00087* (2013.01); *A61B 5/0084* (2013.01); *A61B 5/4255* (2013.01); *A61B 2562/043* (2013.01)

(58) Field of Classification Search
CPC ............ A61B 1/00009; A61B 1/00087; A61B 1/00177; A61B 1/00181; A61B 1/00193; A61B 2562/043; A61B 5/0084; A61B 5/065; A61B 5/1032; A61B 5/4255
USPC .......................................... 600/117; 348/140
See application file for complete search history.

(56) References Cited

U.S. PATENT DOCUMENTS

| | | | | |
|---|---|---|---|---|
| 5,512,940 A | * | 4/1996 | Takasugi ............... | G06T 7/0012 348/30 |
| 6,387,043 B1 | | 5/2002 | Yoon | |

(Continued)

FOREIGN PATENT DOCUMENTS

| | | |
|---|---|---|
| KR | 10-2002-0035588 | 5/2000 |
| KR | 10-2003-0033177 | 5/2003 |

(Continued)

*Primary Examiner* — John P Leubecker
*Assistant Examiner* — Arnaldo Torres Diaz
(74) *Attorney, Agent, or Firm* — NSIP Law

(57) ABSTRACT

An endoscope using depth information and a method for detecting a polyp based on the endoscope using the depth information are provided. The endoscope using the depth information may generate an irradiated light signal including a visible light, obtain depth information based on the irradiated light signal and a reflected light signal obtained through the irradiated light signal being reflected off of an intestine wall, generate a depth image inside the intestine wall based on the depth information, and detect a polyp located on the intestine wall based on the depth image.

23 Claims, 13 Drawing Sheets

(51) Int. Cl.
*A61B 5/103* (2006.01)
*A61B 5/00* (2006.01)

(56) References Cited

U.S. PATENT DOCUMENTS

| | | | | |
|---|---|---|---|---|
| 7,385,708 | B2 * | 6/2008 | Ackerman | A61B 1/042 356/603 |
| 7,865,231 | B2 * | 1/2011 | Tearney | A61B 1/00165 600/407 |
| 8,451,456 | B2 * | 5/2013 | Babayoff | A61B 1/00009 250/559.4 |
| 8,482,722 | B2 * | 7/2013 | Min | G01S 7/491 356/4.01 |
| 8,581,970 | B2 * | 11/2013 | Yamazaki | A61B 1/0638 348/65 |
| 8,675,207 | B2 * | 3/2014 | Babayoff | A61B 1/00009 250/559.4 |
| 8,780,176 | B2 * | 7/2014 | Yelin | H04N 5/2256 348/42 |
| 8,864,655 | B2 * | 10/2014 | Ramamurthy | A61B 5/06 600/117 |
| 8,928,890 | B2 * | 1/2015 | Nebosis | A61B 5/0066 356/497 |
| 9,047,681 | B2 * | 6/2015 | Choi | G06T 3/4007 |
| 2003/0193657 | A1 * | 10/2003 | Uomori | G01B 11/25 356/3.1 |
| 2004/0176685 | A1 * | 9/2004 | Takizawa | A61B 1/00036 600/424 |
| 2004/0236228 | A1 * | 11/2004 | Stoltz | A61B 1/05 600/473 |
| 2005/0092897 | A1 * | 5/2005 | Schwarte | G01J 9/00 250/214.1 |
| 2005/0219552 | A1 * | 10/2005 | Ackerman | A61B 1/042 356/603 |
| 2007/0064239 | A1 * | 3/2007 | Fujita | G02B 21/0056 356/479 |
| 2008/0208006 | A1 * | 8/2008 | Farr | A61B 1/0607 600/178 |
| 2008/0281154 | A1 * | 11/2008 | Gono | A61B 1/0638 600/109 |
| 2009/0147999 | A1 * | 6/2009 | Maeda | A61B 1/00009 382/106 |
| 2009/0253954 | A1 * | 10/2009 | Katayama | A61B 1/045 600/103 |
| 2010/0294917 | A1 * | 11/2010 | Morgan | G01P 5/26 250/214 A |
| 2011/0202310 | A1 * | 8/2011 | Min | G01S 17/10 702/166 |
| 2012/0056986 | A1 | 3/2012 | Popovic | |
| 2012/0113306 | A1 * | 5/2012 | Dai | H04N 5/378 348/308 |
| 2013/0083309 | A1 * | 4/2013 | Shim | G01S 7/497 356/4.07 |
| 2013/0187689 | A1 * | 7/2013 | Choi | H03L 7/093 327/157 |
| 2013/0251243 | A1 * | 9/2013 | Shim | G06T 7/0075 382/154 |
| 2013/0258099 | A1 * | 10/2013 | Ovsiannikov | G01B 11/026 348/140 |
| 2013/0301907 | A1 * | 11/2013 | Shim | G06K 9/00201 382/154 |
| 2013/0301908 | A1 * | 11/2013 | Shim | G06T 5/005 382/154 |
| 2014/0022349 | A1 * | 1/2014 | Kang | G01N 21/55 348/46 |
| 2014/0078459 | A1 * | 3/2014 | Kim | G02F 1/1333 349/193 |
| 2014/0241644 | A1 * | 8/2014 | Kang | G06T 5/002 382/260 |

FOREIGN PATENT DOCUMENTS

| | | |
|---|---|---|
| KR | 10-2004-0094936 | 11/2004 |
| KR | 10-2007-0018946 | 2/2007 |
| KR | 10-2011-0025263 | 3/2011 |
| KR | 10-2011-0048159 | 5/2011 |
| KR | 10-2011-0104234 | 9/2011 |

* cited by examiner

FIG. 7

| G | B | G | B |
|---|---|---|---|
| R | G | R | G |
| G | B | G | B |
| R | G | R | G |

INCIDENT WAVE

REFLECTED WAVE

ENDOSCOPE USING DEPTH INFORMATION AND METHOD FOR DETECTING POLYP BASED ON ENDOSCOPE USING DEPTH INFORMATION

CROSS-REFERENCE TO RELATED APPLICATIONS

This application claims the priority benefit of Korean Patent Application No. 10-2013-0000570, filed on Jan. 3, 2013, in the Korean Intellectual Property Office, the disclosure of which is incorporated herein by reference.

BACKGROUND

1. Field

Example embodiments relate to an endoscope using depth information and method for detecting a polyp based on the endoscope.

2. Description of the Related Art

An endoscope is an apparatus for diagnosing an image frequently used during health examinations because the endoscope provides an image almost identical to an image observed by a naked eye of a human. Recently, use of the endoscope has contributed to early diagnosis and early treatment of diseases by removing a polyp upon detection of the polyp during diagnosis.

Detecting whether the polyp is located on an intestine wall may be an issue because rotating the endoscope through a range of varied angles to obtain images is difficult due to an intestine being narrower than a stomach.

SUMMARY

In an aspect of one or more embodiments, there is provided an endoscope using depth information, the endoscope including a light source unit to generate an irradiated light signal including a visible light, a sensing unit to obtain depth information, based on the irradiated light signal and a reflected light signal generated through the irradiated light signal being reflected off of an intestine wall, and an image processing unit to generate a depth image inside the intestine wall based on the depth information, and detect a polyp located on the intestine wall based on the depth image.

The light source unit may generate the irradiated light signal modulated to a frequency of the visible light while being disposed around the sensing unit.

The sensing unit may obtain color information based on the irradiated light signal and the reflected light signal.

The sensing unit may include a converting unit to convert the reflected light signal to an electrical signal, an electric charge measuring unit to use signals obtained from phase converting of the irradiated light signal as a control signal for operating a switch, and measure an electric charge accumulated by the electrical signal in a capacitor connected to the switch for a plurality of phases, and a strength and phase calculating unit to calculate a phase and an average strength of the reflected light signal based on the electric charge measured for the plurality of phases.

The sensing unit may further include a three-dimensional (3D) information determining unit to determine depth information for a pixel based on the phase of the reflected light signal calculated for the pixel, and determine the average strength of the reflected light signal calculated for the pixel to be color information for the pixel.

The electric charge measuring unit may use four signals obtained from phase converting of the irradiated light signal in a unit of $\pi/2$ radians as a control signal for operating a switch, and measure the electric charge accumulated by the electrical signal in the capacitor connected to the switch, with respect to the four phases.

The light source unit may generate an irradiated light signal further including an infrared ray.

The light source unit and the sensing unit may be disposed on at least one of a front portion of the endoscope initially entering an intestine and a side portion of the endoscope.

The endoscope using the depth information may further include a control unit to calculate a distance from a surgical tool disposed on the front portion of the endoscope initially entering the intestine to a position of a polyp detected when the polyp is detected based on the depth information obtained from the sensing unit disposed on the side portion of the endoscope.

The image processing unit may include a down-sampling unit to down-sample the depth image inside the intestine wall in various scales, and a determining unit to determine that the polyp is located at a position of a corresponding pixel when a depth value of a pixel in the down-sampled depth image is determined to be less than a depth value of neighboring pixels, by an amount differing from a threshold value.

The image processing unit may include a modeling unit to model a shape of an interior of the intestine wall based on average depth information of the obtained depth information, and a determining unit to determine that the polyp is located at a position of a corresponding pixel when a matching error is greater than a threshold value through matching the obtained depth information and the modeled shape of the interior of the intestine wall for a pixel.

The light source unit may generate a pulse of the irradiated light signal once per predetermined period.

The endoscope using the depth information may further include a surgical tool disposed on a front portion of the endoscope initially entering an intestine.

The endoscope may include a head portion on which the surgical tool is disposed, and a supporting portion that bends in all directions while supporting the head portion.

In an aspect of one or more embodiments, there is provided an endoscope using depth information, the endoscope including a light source unit to generate an irradiated light signal including an infrared ray, a sensing unit to obtain depth information, based on the irradiated light signal and a reflected light signal generated through the irradiated light signal being reflected off of an intestine wall, and an image processing unit to generate a depth image inside the intestine wall based on the depth information, and detect a polyp located on the intestine wall based on the depth image.

In an aspect of one or more embodiments, there is provided a method for detecting a polyp based on an endoscope using depth information, the method including generating an irradiated light signal including a visible light, obtaining depth information, through a color/depth sensor, based on the irradiated light signal and a reflected light signal generated through the irradiated light signal being reflected off of an intestine wall, generating a depth image inside the intestine wall based on the depth information, and detecting a polyp located on the intestine wall based on the depth image.

The generating of the irradiated light signal may include generating an irradiated light signal further including an infrared ray, and obtaining color information and depth information based on the irradiated light signal and the reflected light signal.

The obtaining of the depth information may include converting the reflected light signal into an electrical signal, using signals obtained through phase converting of the irradiated light signal as a control signal for operating a switch, and measuring an electric charge accumulated by the electrical signal in a capacitor connected to the switch for a plurality of phases, and calculating a phase and an average strength of the reflected light signal based on the electric charge measured for the plurality of phases.

The obtaining of the depth information may further include determining depth information for a pixel based on a phase of the reflected light signal calculated for the pixel, and determining an average strength of the reflected light signal calculated for the pixel to be color information for the pixel.

The method for detecting the polyp based on the endoscope using the depth information may further include calculating a distance from a surgical tool disposed on a front portion of the endoscope initially entering an intestine to a position of a polyp detected when the polyp is detected based on the depth information obtained from the color/depth sensor disposed on a side portion of the endoscope.

The detecting of the polyp may include down-sampling a depth image inside the intestine wall in various scales, and determining that the polyp is located at a position of a corresponding pixel when a depth value of a pixel in the down-sampled depth image is less than a depth value of neighboring pixels, by an amount differing from a threshold value.

The generating of the depth image may include modeling a shape of the interior of the intestine wall based on an average of the depth information obtained.

The detecting of the polyp may include determining that the polyp is located at a position of a corresponding pixel, when matching error is greater than a threshold value, through matching the obtained depth information and the modeled shape of the interior of the intestine wall.

In an aspect of one or more embodiments, there is provided a method for detecting a polyp based on an endoscope using depth information, the method including obtaining depth information, using a color/depth sensor, based on an irradiated light signal and a reflected light signal generated by the irradiated light signal being reflected off of an intestine wall of an intestine; generating a depth image inside the intestine wall based on the depth information; and detecting a polyp located on the intestine wall based on the depth image.

According to an aspect of one or more embodiments, there is provided at least one non-transitory computer readable medium storing computer readable instructions to implement methods of embodiments.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which:

FIG. 7 illustrates a pattern located on a color/depth sensor of an endoscope using depth information according to example embodiments;

DETAILED DESCRIPTION

Figure 1:
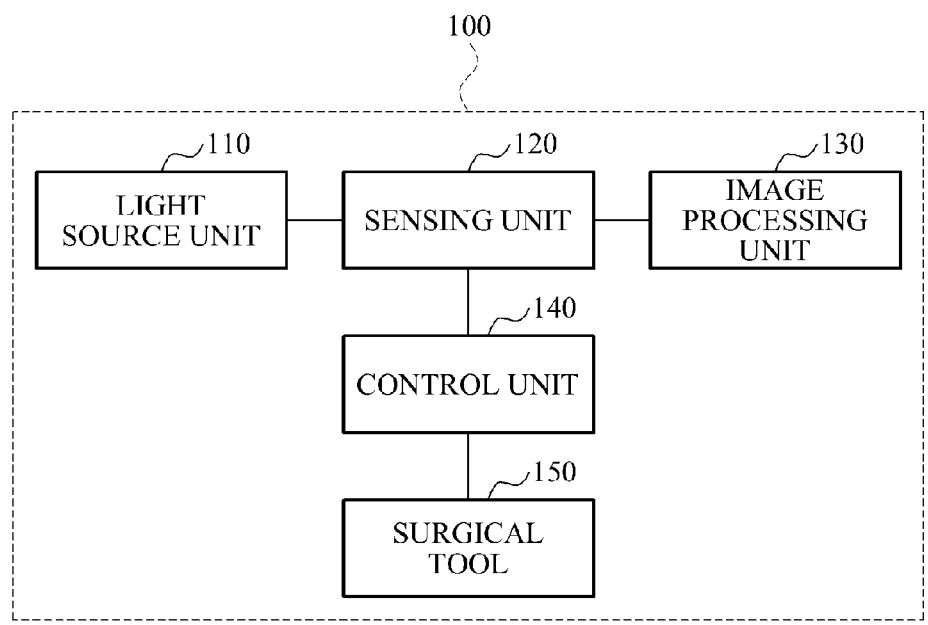
FIG. 1 illustrates an endoscope using depth information according to example embodiments.

Reference will now be made in detail to embodiments, examples of which are illustrated in the accompanying drawings, wherein like reference numerals refer to the like elements throughout. Embodiments are described below to explain the present disclosure by referring to the figures.

FIG. 1 illustrates an endoscope 100 using depth information according to example embodiments.

Referring to FIG. 1, the endoscope 100 using the depth information may include a light source unit (light source) 110, a sensing unit (sensor) 120, an image processing unit (image processor) 130, a control unit (controller) 140, and a surgical tool 150.

The light source unit 110 may generate an irradiated light signal including a visible light. The irradiated light signal may refer to a light signal irradiated from the light source unit 110. The light source unit 110 may generate an irradiated light signal including an infrared ray. The visible light may be used for obtaining depth information because an interior of a body is not exposed to an additional light source aside from the light source unit 110. The light source unit 110 may generate the visible light and the infrared ray. The light source unit 110 may generate the irradiated light signal using a light emitting diode (LED) or a laser diode (LD).

The light source unit 110 may be disposed around the sensing unit 120. The light source unit 110 may be disposed on a front portion of the endoscope 100 initially entering an intestine. The sensing unit 120 may be disposed adjacent to the front portion of the endoscope 100 initially entering the intestine and the light source unit 110. The light source unit 110 and the sensing unit 120 may be disposed on a side portion of the endoscope 100.

The light source unit 110 disposed on the front portion of the endoscope 100 may generate an irradiated light signal in a direction of which the endoscope 100 is progressing, and the sensing unit 120 may obtain depth information in the progressing direction of the endoscope 100. In another example embodiment, when the visible light is used as the irradiated light signal in the light source unit 110, the sensing unit 120 may obtain color information and the depth information in the progressing direction of the endoscope 100. In another example embodiment, the sensing unit 120 may obtain the color information and the depth information in the progressing direction of the endoscope 100 when the light source unit 110 generates the irradiated light signal including the visible light and the infrared ray.

The light source unit 110 disposed on the side portion of the endoscope 100 may generate an irradiated light signal in a direction vertical to the progressing direction of the endoscope 100, and the sensing unit 120 may obtain at least one of the color information and the depth information in the direction vertical to the progressing direction of the endoscope 100.

The light source unit 100 may generate an irradiated light signal modulated to a frequency of the visible light. The light source unit 110 may generate an irradiated light signal modulated to a frequency of the infrared ray.

The sensing unit 120 may obtain depth information of a pixel, based on an irradiated light signal and a reflected light signal generated through the irradiated light signal being reflected off of an intestine wall. The sensing unit 120 may obtain the color information and the depth information of the pixel, based on the irradiated light signal and the reflected light signal when the visible light is used as the irradiated light signal in the light source unit 110.

The sensing unit 120 may use a plurality of signals generated through phase converting of the irradiated light signal as a control signal for operating a switch. The control unit 140 may generate the plurality of signals by phase converting of the irradiated light signal. For example, the control unit 140 may generate a signal obtained through phase converting of the irradiated light signal to $\pi/2$ radians, a signal obtained through phase converting of the irradiated light signal to $\pi$ radians, and a signal obtained through phase converting of the irradiated light signal to $3\pi/2$ radians, in a unit of $\pi/2$ radians.

The sensing unit 120 may store the reflected light signal in a capacitor for a plurality of phases through turning a switch ON/OFF, using the signals generated through phase converting as control signals for operating the switch. The sensing unit 120 may turn the switch ON/OFF for the plurality of phases. An example in which the switch is turned ON/OFF for the plurality of phases will further be described with reference to FIG. 3A. The sensing unit 120 may measure an electric charge stored in the capacitor by the reflected light signal for the plurality of phases.

The electric charge stored in a pixel may be calculated for the plurality of phases, by convoluting the signals obtained through phase converting and the reflected light signal.

The sensing unit 120 may calculate a phase and an average strength of the reflected light signal, using the electric charge measured for the plurality of phases. In this instance, the average strength of the reflected light signal may correspond to a color value of a pixel, and the phase of the reflected light signal may correspond to a depth value of a pixel. The sensing unit 120 may obtain color information and depth information of a pixel from a strength and a phase of the reflected light signal.

The light source unit 110 may be located at least one of the front portion of the endoscope 100 initially entering the intestine and the side portion of the endoscope 100.

The image processing unit 130 may generate a depth image inside the intestine wall, based on the depth information obtained from the sensing unit 120. The depth image may be generated inside the intestine wall may be generated based on the depth information obtained from the sensing unit 120, because the light source unit 110 and the sensing unit 120 are located on the front portion and the side portion of the endoscope 100.

The image processing unit 130 may detect a polyp located on the intestine wall based on the depth image. For example, the image processing unit 130 may determine that the polyp is generated in a pixel in which a difference between depth values of neighboring pixels in the depth image inside the intestine wall is greater than a predetermined threshold value because the depth values of the neighboring pixels in the depth image inside the intestine wall in which the polyp is not generated may be similar to one another.

The control unit 140 may calculate a distance from the surgical tool 150 disposed on the front portion of the endoscope 100 to a location of a polyp detected when the polyp is detected based on the depth information obtained from the sensing unit 120 disposed on the side portion of the endoscope 100. A distance between the surgical tool 150 disposed on the front portion of the endoscope 100 and the sensing unit 120 disposed on the side portion of the endoscope 100 may be calibrated in advance. Accordingly, the control unit 140 may calculate the distance from the surgical tool 150 to the polyp, based on the information calibrated in advance when the polyp is detected from a predetermined sensing unit 120 disposed on the side portion of the endoscope 100. A distance by which the surgical tool 150 is to be retracted may be determined automatically to remove the polyp, based on the distance calculated in the control unit 140.

The surgical tool 150 may be disposed on the front portion of the endoscope 100 initially entering the intestine. The surgical tool 150 may include a pair of forceps, a laser, and the like, for removing the polyp.

The light source unit 110 may generate a pulse of the irradiated light signal continuously during a period. For example, the light source unit 110 may generate the irradiated light signal in a continuous wave amplitude modulation scheme.

The light source unit 110 may generate a pulse of the irradiated light signal once per a predetermined period. For example, the light source unit 110 may generate the irradiated light signal in a direct pulse scheme.

When the irradiated light signal generated in the continuous wave amplitude modulation scheme is used, erroneous depth information may be obtained through a signal reflected off of an a different object being detected along with the irradiated light signal, for a pixel. In an instance of the direct pulse scheme, an issue of light being reflected off of several objects may decrease by irradiating a single light signal in a form of a pulse over a set period.

Figure 2:
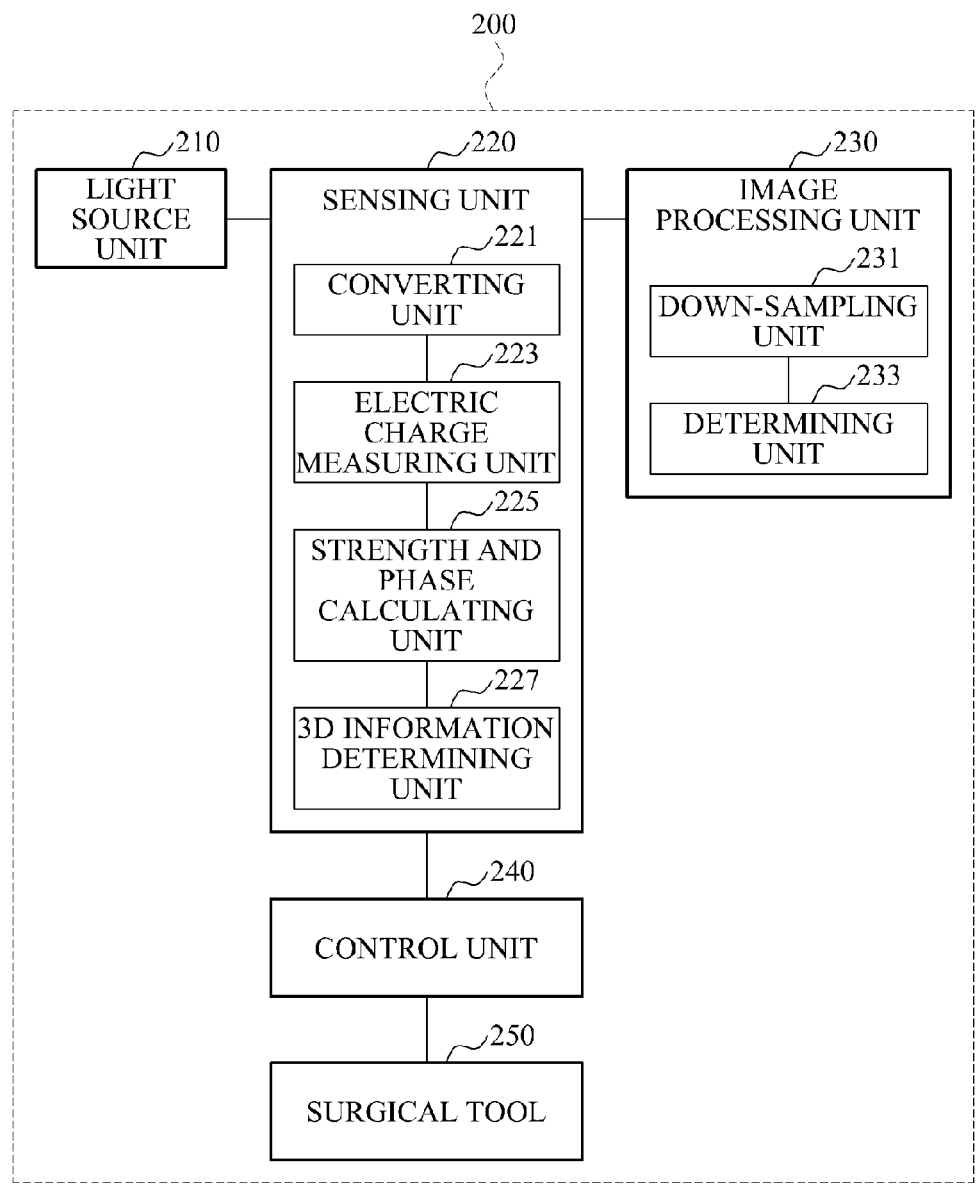
FIG. 2 illustrates an endoscope using depth information according to other example embodiments.

FIG. 2 illustrates an endoscope 200 using depth information according to other example embodiments.

Referring to FIG. 2, the endoscope 200 may include a light source unit 210, a sensing unit 220, an image processing unit 230, a control unit 240, and a surgical tool 250.

The light source unit 210 may generate an irradiated light signal including at least one of a visible light and an infrared ray. The light source unit 210 may irradiate only the visible light. The visible light may be used for obtaining depth information because an interior of a body is not exposed to an additional light source aside from the light source unit 210. The light source unit 210 may generate the irradiated light signal using an LED or an LD.

The light source unit 210 may be disposed on a front portion of the endoscope 200 initially entering an intestine. The sensing unit 220 may be disposed adjacent to the front portion of the endoscope 200 initially entering the intestine and the light source unit 210. The light source unit 210 and the sensing unit 220 may be disposed on a side portion of the endoscope 200.

The sensing unit 220 may obtain depth information of a pixel, based on an irradiated light signal and a reflected light signal generated through the irradiated light signal being reflected off of an intestine wall. The sensing unit 220 may obtain color information and the depth information of the pixel, based on the irradiated light signal and the reflected light signal when the visible light is used as the irradiated light signal in the light source unit 210. The sensing unit 220 may refer to a color/depth sensor in which a single lens is provided.

The sensing unit 220 may include a converting unit (converter) 221, an electric charge measuring unit (electric charge measurer) 223, a strength and phase calculating unit (strength and phase calculator) 225, and a three-dimensional (3D) information determining unit (three-dimensional (3D) information determiner) 227.

When the irradiated light signal generated from the light source unit 210 is g(t), and a reflected light signal obtained from the irradiated light signal being reflected off of an intestine wall and subsequently returning to a pixel is s(t), g(t) and s(t) may be represented mathematically as follows.

$$g(t)=1+\sin(2\pi ft)$$

$$g(t)=1+\sin(2\pi ft)$$

Here, f denotes a modulation frequency of the irradiated light signal, and t denotes a time. $\phi$ denotes a phase of the reflected light signal and may be proportional to a time-of-flight of the reflected light signal. d denotes a distance over which the reflected light signal moves. d may be calculated by the following equation. Depth information, being a distance from the pixel of the sensing unit 220 to the intestine wall, may be calculated from d.

$$d = \frac{c\phi}{4\pi f}$$

Here, c denotes the speed of light.

The converting unit 221 may convert the reflected light signal to an electric signal for a pixel. The converting unit 221 may be configured by a photo diode. The reflected light signal received in a form of the photo diode may be converted to the electric signal. The electric signal may be permitted to a capacitor located for the pixel, and charge an electric charge in the capacitor.

The electric charge measuring unit 223 may use signals obtained through phase converting of the irradiated light signal as control signals for operating a switch, and measure an electric charge accumulated by the electric signal in the capacitor connected to the switch for the plurality of phases. The electric charge measuring unit 223 may turn the switch ON/OFF based on the signal obtained through phase converting of the irradiated light signal, and accumulate an electric charge in the capacitor by the electric signal when the switch is turned ON. The electric charge measuring unit 223 may measure the electric charge accumulated in the capacitor for the plurality of phases.

The electric charge measuring unit 223 may measure the electric charge stored in the capacitor for the plurality of phases through an optical shutter of differing phases. Alternatively, the electric charge measuring unit 223 may measure the electric charge stored in the capacitor based on an operation of the switch controlled by the electric signal inside a pixel. For example, the electric signal inside the pixel may be represented as follows. The electric signal inside the pixel may be represented using the irradiated light signal. When the irradiated light signal is g0(t), g0.5π(t), gπ(t), and g1.5π(t) may be signals obtained through phase converting from g0(t) in a unit of π/2 radians. The signals obtained through phase converting of the irradiated light signal may be used for controlling the operation of the switch connecting the converting unit 221 and the capacitor.

$$g_0(t)=1+\sin(2\pi ft)$$

$$g_{0.5\pi}(t)=1-\cos(2\pi ft)$$

$$g_\pi(t)=1-\sin(2\pi ft)$$

$$g_{1.5\pi}(t)=1+\cos(2\pi ft)$$

For example, when the electric charge measuring unit 223 permits the four signals g0(t), g0.5π(t), gπ(t), and g1.5π(t) obtained through phase converting of the irradiated signal in a unit of π/2 radians to the switch, the switch may be turned ON/OFF for the plurality of phases. As an example, a single pixel may be configured by two capacitors and two switches. The converting unit 221 and the respective capacitors may be connected by the switches. The respective switches may be turned ON/OFF at a 0 phase and a π phase, and turned ON/OFF at a 0.5π phase and a 1.5π phase. The electric charge measuring unit 223 may measure an electric charge accumulated in the respective capacitors through the respective switches being turned on at the 0 phase and the π phase, and discharge the electric charge stored in the respective capacitors. The electric charge measuring unit 223 may measure the electric charge accumulated in the respective capacitors through the respective switches being turned ON at the 0.5π phase and the 1.5π phase. The electric charge measuring unit 223 may measure the electric charge stored in the capacitor at the 0 phase, the 0.5π phase, the π phase, and the 1.5π phase.

The electric charge for the four phases may be calculated by convoluting the four signals, being g0(t), g0.5π(t), gπ(t), and g1.5π(t) obtained through phase converting of the irradiated light signal and the electric signal s(t), from t=0 to a period T.

The electric charge for the four phases may be represented by the following equations.

$$c(0)=(B+0.5A\cos\phi)\times T$$

$$c(0.5\pi)=(B+0.5A\sin\phi)\times T$$

$$c(\pi)=(B-0.5A\cos\phi)\times T$$

$$c(1.5\pi)=(B-0.5A\sin\phi)\times T$$

The strength and phase calculating unit 225 may calculate an average strength and a phase of a reflected light signal, based on electric charges measured for the plurality of phases.

The strength and phase calculating unit 225 may calculate B corresponding to the average strength of the reflected light signal and $\phi$, being a phase of s(t), using the electric charges measured in the electric charge measuring unit 223.

$$B = 0.25 \times (c(0) + c(0.5\ \pi) + c(\pi) + c(1.5\ \pi))$$

$$\phi = \tan^{-1}\left(\frac{c(0.5\ \pi) - c(1.5\ \pi)}{c(0) - c(\pi)}\right)$$

When a white light is irradiated from the light source unit 210, the value B of the aforementioned equation denotes an average strength of a reflected light signal admitted to a pixel having a color value, and cp denotes a value proportional to a depth value, and therefore, the 3D information determining unit 227 may obtain color information and depth information simultaneously.

The 3D information determining unit 227 may determine a strength of the reflected light signal obtained through the irradiated light signal being reflected off of an intestine wall for a pixel to be color information for the pixel, and determine depth information for a pixel, based on a phase of the reflected light signal obtained through the irradiated light signal being reflected off of the intestine wall for the pixel. As an example, the 3D information determining unit 227 may determine a strength of the reflected light signal to be the color information, and determine the depth information based on the phase of the reflected light signal when the light source unit 210 generates an irradiated light signal including the visible light. As another example, the 3D information determining unit 227 may determine only the depth information based on the phase of the reflected light signal when the light source unit 210 generates an irradiated light signal including an infrared ray only.

The image processing unit 230 may generate a depth image inside the intestine wall based on the depth information obtained from the sensing unit 220. The depth image inside the intestine wall may be generated using the depth information obtained from the sensing unit 220 because the light source unit 210 and the sensing unit 220 are disposed on a front portion and a side portion of the endoscope 200.

The image processing unit 230 may detect a polyp located on the intestine wall based on the depth image.

The image processing unit 230 may include a down-sampling unit 231 and a determining unit (determining unit) 233.

The down-sampling unit (down-sampler) 231 may down-sample the depth image inside the intestine wall in various scales. The down-sampling unit 231 may down-sample the depth image by calculating an average depth value of pixels through grouping the pixels. In this instance, scales may differ depending on a number of pixels being grouped.

The determining unit (determiner) 233 may determine that the polyp is located at a position of a corresponding pixel when a depth value of a pixel in the down-sampled depth image is determined to be less than a depth value of neighboring pixels, by an amount differing from a threshold value. The depth value of a portion at which the polyp is generated may have a depth value less than a depth value of a portion at which the polyp is not generated. The threshold value may be determined based on a size of the polyp that distinguishes the polyp. As an example, the depth value may be a distance from a pixel to an intestine wall or a distance form a pixel to the polyp.

The control unit 240 may calculate a distance from the surgical tool 250 disposed on the front portion of the endoscope 200 to the position of a polyp detected when the polyp is detected based on the depth information obtained from the sensing unit 220 disposed on the side portion of the endoscope 200. A distance between the surgical tool 250 disposed on the front portion of the endoscope 200 and the sensing unit 220 disposed on the side portion of the endoscope 200 may be calibrated in advance. Accordingly, the control unit 240 may calculate a distance from the surgical tool 250 to the polyp based on the information calibrated in advance when the polyp is detected from a predetermined sensing unit 220 disposed on the side portion of the endoscope 200. A distance by which the surgical tool 250 is to be retracted may be determined automatically to remove the polyp, based on the distance calculated in the control unit 240.

The surgical tool 250 may be disposed on the front portion of the endoscope 200 initially entering the intestine. The surgical tool 250 may include a pair of forceps, a laser, and the like, for removing the polyp.

Figure 3A:
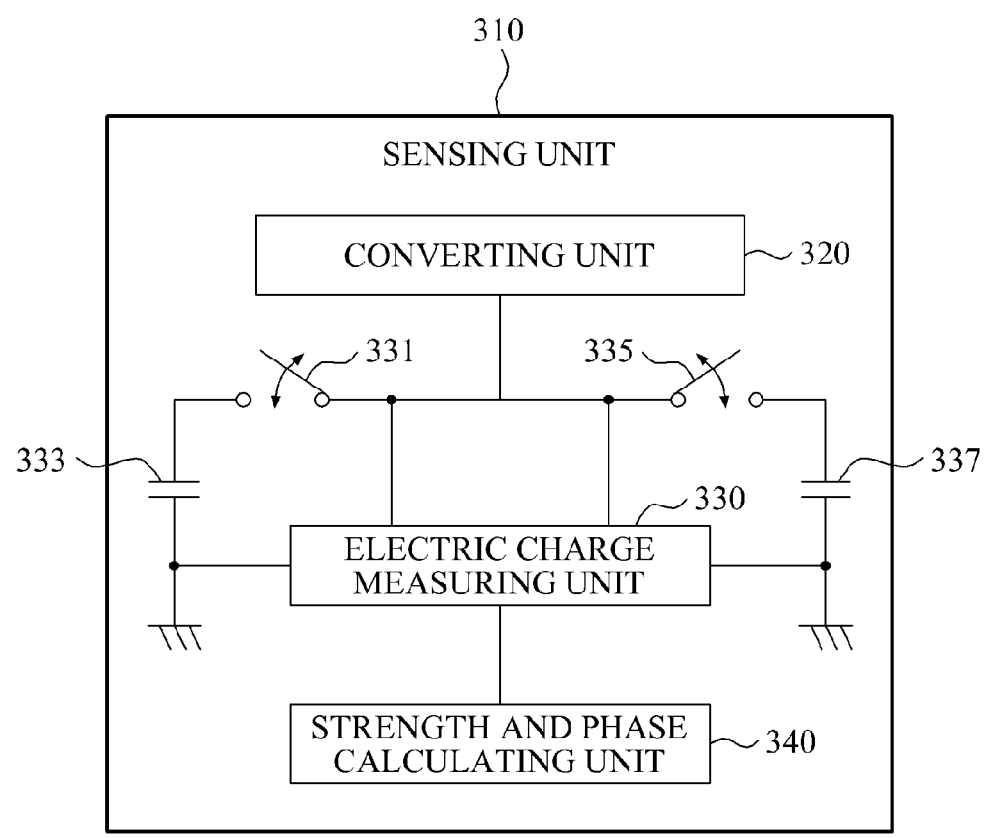
FIG. 3A illustrates a configuration of a sensing unit of an endoscope using depth information according to example embodiments.
Figure 3B:
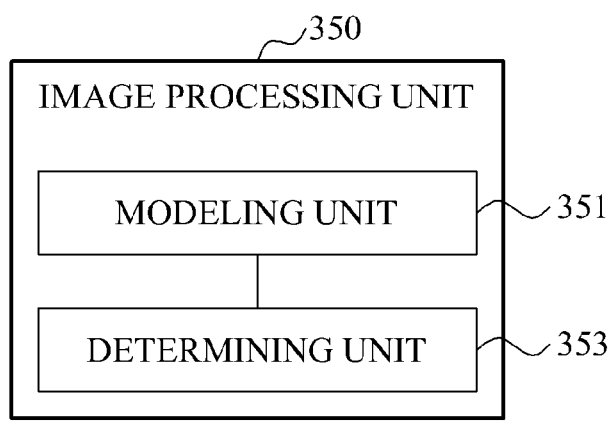
FIG. 3B illustrates a configuration of an image processing unit of the endoscope using the depth information according to example embodiments.

FIG. 3A illustrates a configuration of a sensing unit 310 of an endoscope using depth information according to example embodiments, and FIG. 3B illustrates a configuration of an image processing unit 350 of the endoscope using the depth information according to example embodiments.

Referring to FIG. 3A, the sensing unit 310 of the endoscope using the depth information may include a converting unit 320, an electric charge measuring unit 330, and a strength and phase calculating unit 340.

The converting unit 320 may convert a reflected light signal to an electric signal for a pixel. As an example, the converting unit 320 may be configured by a photo diode. In this example, the reflected light signal received in a form of the photo diode may be converted to the electric signal.

The electric charge measuring unit 330 may use signals obtained through phase converting of the irradiated light signal as control signals for operating switches 331 and 335, and measure an electric charge accumulated by the electric signal in capacitors 333 and 337 connected to the switches 331 and 335 for the plurality of phases. Here, the electric signal may be a signal outputted from the converting unit 320.

For example, the irradiated light signal may be phase converted in a unit of $\pi/2$ radians. Signals obtained through phase converting of the irradiated light signal at a 0 phase, a $0.5\pi$ phase, a $\pi$ phase, and a $1.5\pi$ phase may be generated.

For example, the irradiated light signal at 0 phase may be permitted to the switch 331, and the switch 331 may be turned ON/OFF based on the irradiated light signal at the 0 phase. The irradiated light signal obtained through being phase converted to the $\pi$ phase may be transmitted to the switch 335, and the switch 335 may be turned ON/OFF based on the irradiated light signal obtained through being phase converted to the $\pi$ phase. The electric charge measuring unit 330 may measure an electric charge at the 0 phase by measuring an electric charge accumulated in the capacitor 333. The electric charge measuring unit 330 may measure an electric charge at the $\pi$ phase by measuring an electric charge accumulated in the capacitor 337.

The electric charge measuring unit 330 may discharge an electric charge stored in the capacitors 333 and 337, subsequent to the measuring of the electric charge at the 0 phase and the electric charge at the $\pi$ phase being completed.

The electric charge measuring unit 330 may measure an electric charge at the $0.5\pi$ phase and an electric charge at the $1.5\pi$ phase through the same scheme as above.

Two switches and two capacitors are used in the example of FIGS. 3A and 3B, however, more than two switches and capacitors may be used. Although the irradiated light signal is phase converted in a unit of $\pi/2$ radians, the unit of phase converting may not be limited to $\pi/2$ radians. Examples in which phase converting is performed in various units may also be applied.

The strength and phase calculating unit 340 may calculate an average strength and a phase of a reflected light signal, based on the electric charge measured for the plurality of phases in the electric charge measuring unit 330.

Referring to FIG. 3B, the image processing unit 350 may include a modeling unit (modeler) 351 and a determining unit 353 in the endoscope using the depth information.

The modeling unit 351 may model a form of an interior of an intestine wall, based on average depth information obtained from a color/depth sensor. For example, when the average depth information is 1 centimeter (cm), the modeling unit 351 may model a shape of a circular cylinder of which a radius is 1 cm in the form of the interior of the intestine wall.

The determining unit 353 may determine that a polyp is located at a position of a corresponding pixel when a matching error is greater than a threshold value by matching the form of the interior of the intestine wall modeled, for a pixel. The polyp may be determined to be located in the corresponding pixel when the matching error exceeds the threshold value due to a depth value being less than average depth information, based on a result of the matching of the depth information for the pixel in the form of the interior of the intestine wall modeled. For example, when the average depth information is 1 cm, a depth value matched may be 0.5 cm, thereby, the matching error may be 0.5 cm, and when the threshold value is 0.2 cm, the polyp may be determined to be located in a pixel having the depth value of 0.5 cm because the matching error is greater than the threshold value.

Figure 4:
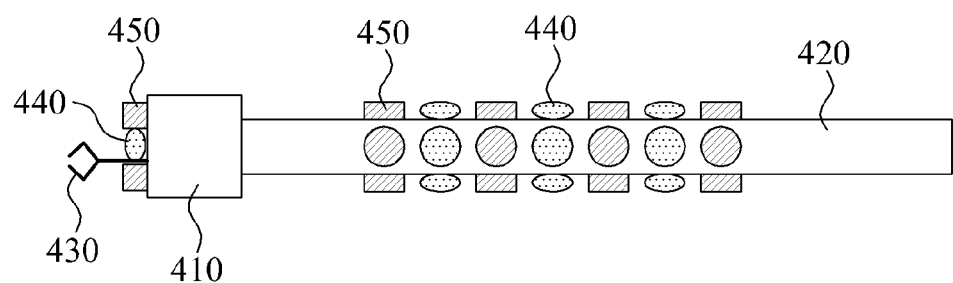
FIG. 4 illustrates a structure of an endoscope using depth information according to example embodiments.

FIG. 4 illustrates a structure of an endoscope using depth information according to example embodiments.

Referring to FIG. 4, the endoscope may support a head portion 410 on which a surgical tool 430 is disposed and a supporting portion 420 supporting the head portion 410 and bending in all directions of 360 degrees.

The surgical tool 430 may be one of various medical devices used to remove a polyp, such as a pair of forceps. For example, the head portion 410 and the supporting portion 420 may include a bundle of glass fibers, and bend in various directions, based on an external stimulus. As another example, the supporting portion 420 may include a bendable portion and an unbendable portion, in response to an external stimulus. The bendable portion may connect the unbendable portions to one another, such as a joint.

A light source 440 may be located at the head portion 410 and the supporting portion 420. The light source 440 may irradiate an irradiated light signal modulated to a frequency of a visible light in a progressing direction of the endoscope and a direction vertical to the progressing direction of the endoscope. The light source 440 may irradiate the irradiated light signal modulated to a frequency of an infrared ray.

A color/depth sensor 450 may be located at the head portion 410 and the supporting portion 420. The color/depth sensor 450 may obtain color information and depth information by receiving a reflected light signal in a pixel unit of the color/depth sensor 450 when the light signal irradiated from the light source 440 is reflected off of an intestine wall.

More particularly, the color/depth sensor 450 may use a plurality of signals generated through phase converting of the irradiated light signal as a control signal for operating a switch, and measure an electric charge accumulated by the reflected light signal in a capacitor connected to the switch, for a plurality of phases.

The color/depth sensor 450 may obtain the color information and the depth information for the pixel, based on an electric charge measured for the plurality of phases.

An image processing unit (not shown) of the endoscope may generate a depth image inside the intestine wall, based on the depth information obtained. The image processing unit (not shown) may compare depth information between neighboring pixels in the depth image, and when a difference between the depth information is greater than a predetermined threshold value, a polyp may be determined to be located in a corresponding pixel. The image processing unit (not shown) may calculate a deviation between the depth information more readily by performing down-sampling to determine whether the polyp is generated and a location of the generation.

Figure 5:
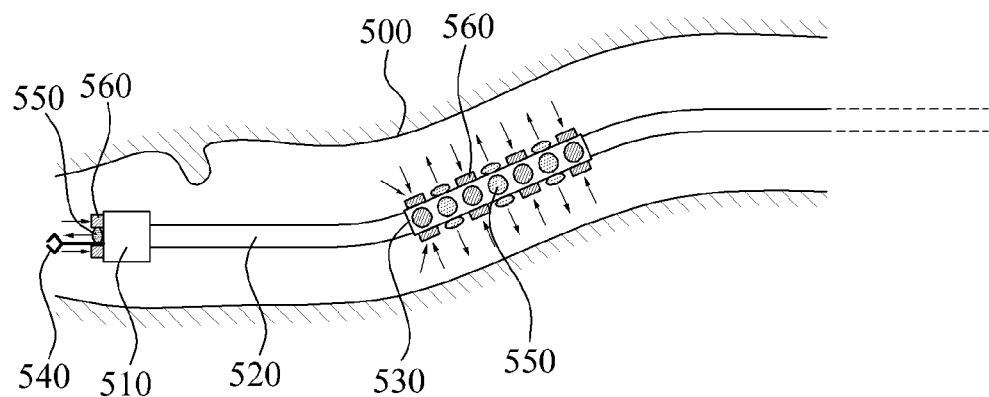
FIG. 5 illustrates a side view of an endoscope using depth information according to example embodiments.

FIG. 5 illustrates a side view of an endoscope using depth information according to example embodiments.

Referring to FIG. 5, the endoscope being inserted inside an intestine 500 may include a head portion 510 and a supporting portion 520 that supports the head portion 510 and bends in all directions, through a range of 360 degrees.

A light source 550 may be located at the head portion 510 and a cover portion 530. The cover portion 530 may be a configuration that covers the supporting portion 520. The light source 550 may irradiate a white light, for example, an irradiated light signal modulated to a frequency of a visible light, in a direction along which the endoscope progresses and in a direction vertical to the direction along which the endoscope progresses. The light source 550 may irradiate the irradiated light signal modulated to a frequency of an infrared ray.

A color/depth sensor 560 may be located at the head portion 510 and the cover portion 530. The color/depth sensor 560 may obtain color information and depth information by receiving a reflected light signal in a pixel unit of the color/depth sensor 560 when the irradiated light signal from the light source 550 is reflected off of an intestine wall. The color information and the depth information may be obtained from the color/depth sensor 560 almost simultaneously with generation of the irradiated light signal because a speed of the reflected light signal received by the color/depth sensor 560 is faster than a progressing speed of the endoscope.

For example, the light source 550 and the color/depth sensor 560 may be attached to the supporting portion 520 directly, and attached to an additional skin, such as the cover portion 530. A plurality of cover portions 530 may be located at the supporting portion 520. Alternatively, one of the plurality of cover portions 530 may move on the supporting portion 520.

The color/depth sensor 560 may be attached to the direction along which the endoscope progresses and to a direction vertical to the direction along which the endoscope progresses. The color/depth sensor 560 attached to the side portion of the endoscope may warn a user of a probability of a polyp by detecting the polyp in advance prior to the color/depth sensor 560 attached to a front portion of the endoscope, observing the polyp. A distance by which the endoscope is to be retracted in order to verify a presence of the polyp by the front color/depth sensor 560 may be determined readily when the polyp is detected in the color/depth sensor 560 disposed to be apart from a surgical tool 540 disposed on the front portion of the endoscope, by a calibrated distance.

For example, the color/depth sensor 560 may use an active time-of flight (TOF) scheme using the light source 550 to obtain depth information. The TOF scheme may obtain the depth information, based on a movement time of the irradiated light signal from the light source 550.

Figure 6:
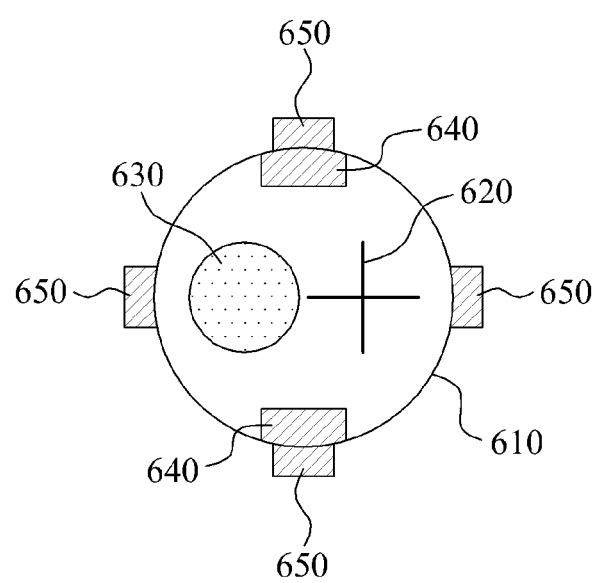
FIG. 6 illustrates a front view of an endoscope using depth information according to example embodiments.

FIG. 6 illustrates a front view of an endoscope using depth information according to example embodiments.

Referring to FIG. 6, a surgical tool 620 may be disposed on a head portion 610 of the endoscope, along with a light source 630 and color/depth sensors 640. As an example, color/depth sensors 650 may be disposed on a side portion of the endoscope.

The light source 630 may generate an irradiated light signal in a progressing direction of the endoscope, and the color/depth sensors 640 may obtain color information and depth information, based on a reflected light signal off of an intestine wall. The color/depth sensors 650 may obtain color information and depth information in the direction along which the endoscope progresses and a direction vertical to the direction along which the endoscope progresses.

Figure 7:
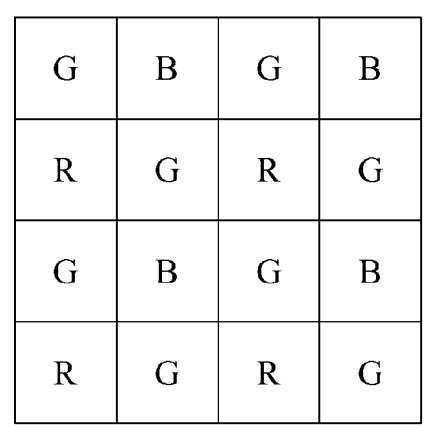

FIG. 7 illustrates a pattern located on a color/depth sensor of an endoscope using depth information according to example embodiments.

The color/depth sensor may be attached to a front portion and a side portion of the endoscope. A pixel of the color/depth sensor may have a pixel structure of a color camera generally used. The pixel of the color/depth sensor may have a pixel structure of a ToF camera.

An electric charge for a plurality of phases in a pixel may be measured in an optical shutter scheme when the pixel structure of the general color camera is used.

Depth information and color information may be obtained concurrently by disposing a Bayer pattern on a pixel when the pixel structure of the ToF camera is used.

The pattern of FIG. 7 illustrates an example of the Bayer pattern. The Bayer pattern of FIG. 7 may be used for obtaining color information and depth information with respect to a pixel in a combination of a single red (R), two greens (G), and a single blue (B).

Figure 8:
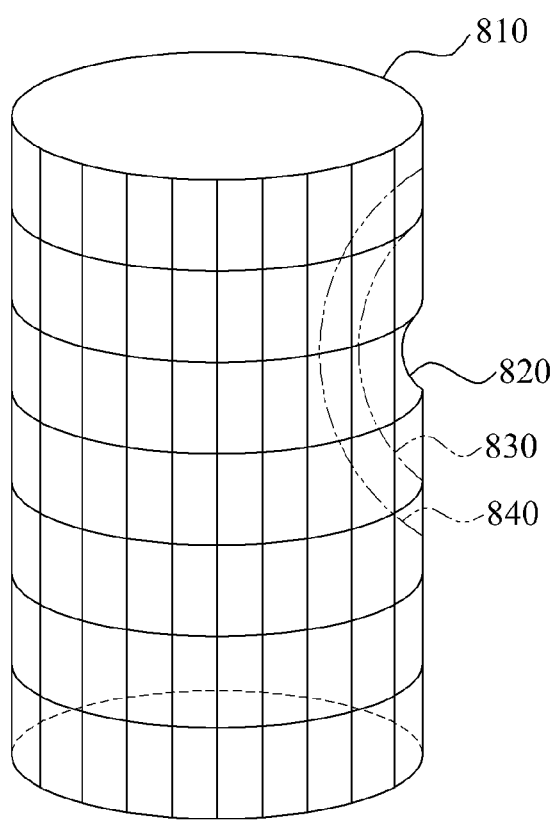
FIG. 8 illustrates a shape of a depth image generated by an endoscope using depth information according to example embodiments.

FIG. 8 illustrates a shape of a depth image 810 generated by an endoscope using depth information 820 according to example embodiments.

Referring to FIG. 8, an image processing unit of the endoscope may generate the depth image 810, based on the depth information obtained from a color/depth sensor. The image processing unit of the endoscope may down-sample the depth image 810 in various scales. The image processing unit may determine that a polyp is generated at a location of a pixel having the depth information 820 when the depth information 820 of a single pixel is substantially less than depth information of a neighboring pixel in the depth image down-sampled.

The down-sampling may occur in a manner such that an average depth value of neighboring pixels being grouped is calculated. The depth information 820 may be displayed as depth information 830 when the down-sampling is performed on the neighboring pixels including the pixel having the depth information 820. The depth information 830 may be displayed as depth information 840 when the down-sampling is performed to include a greater number of pixels. The down-sampling in various scales allows for a determination as to whether a polyp is generated may be performed readily. A location of the generation of the polyp may be estimated more precisely as a number of down-sampling becomes fewer.

As another example, the polyp may be determined to be generated in a pixel having a greater value, using a Gaussian filter, for example, Laplacian of Gaussian (LoG) in a depth image in various scales because the polyp is generated in a circular shape generally.

Figure 9:
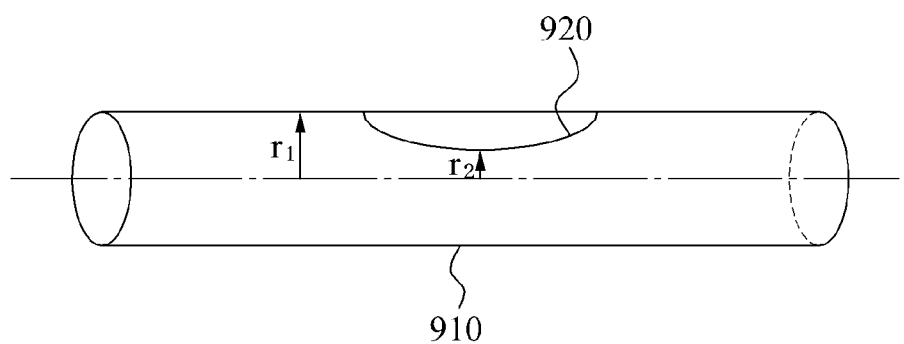
FIG. 9 illustrates a shape of a depth image modeled in an endoscope using depth information according to example embodiments.

FIG. 9 illustrates a shape of a depth image modeled in an endoscope using depth information according to example embodiments.

Referring to FIG. 9, an image processing unit of the endoscope may model a shape 910 of an interior of an intestine wall, based on average depth information $r_1$ obtained from a color/depth sensor. The image processing unit may match the shape 910 modeled and depth information for a pixel obtained, and determine that a polyp is generated in a pixel of which a matching error is greater than a predetermined threshold value. For example, a polyp 920 may be determined to be generated when a matching error $r_1$-$r_2$ of a pixel is greater than a predetermined threshold value. The image processing unit may detect a generation of the polyp 920 more precisely, based on a setting of a threshold value.

Figure 10A:
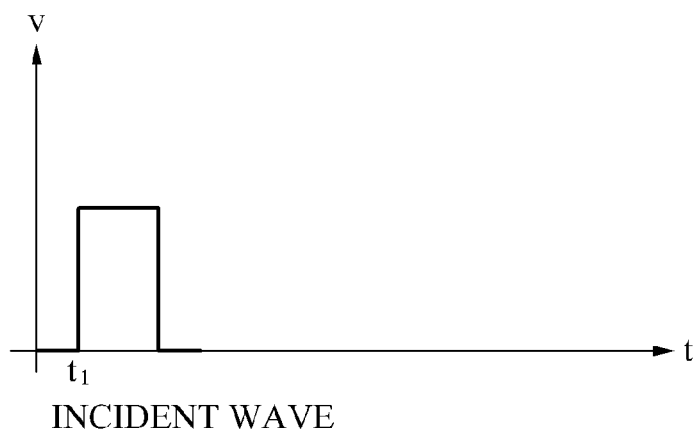
FIGS. 10A and 10B illustrate a scheme for irradiating a light signal from an endoscope using depth information according to example embodiments.
Figure 10B:
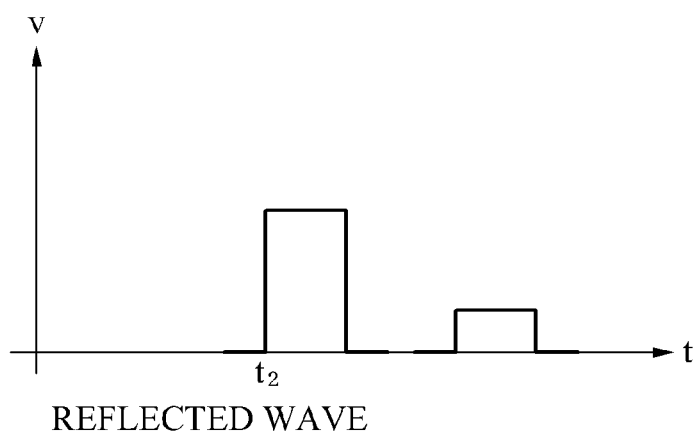

FIGS. 10A and 10B illustrate a scheme for irradiating a light signal from an endoscope using depth information according to example embodiments.

A distance from the color/depth sensor to an intestine wall may be calculated by a light source of the endoscope irradiating a pulse of a light signal once per period, and by a color/depth sensor detecting a pulse signal returning through being reflected. Erroneous depth information may be calculated because signals returning as a result of being reflected off of different portions of the intestine wall may be received in a pixel of the color/depth sensor concurrently when a plurality of light signals is irradiated in a single period. A scheme for irradiating a single pulse signal in a single period may be used in a scheme for calculating the depth information more precisely by reducing a probability of being reflected off of several portions.

Referring to FIG. 10, an endoscope according to an example embodiment may calculate a distance between a sensor and an intestine wall, using a reflected wave of a light signal of (b) returning through being reflected off of an intestine wall, subsequent to irradiating a light signal of (a) in a form of a pulse. The endoscope may calculate a distance based on an initial receiving point $t_2$ of the reflected wave returning through being reflected off of an irradiating point $t_1$ of an incident wave.

Figure 11:
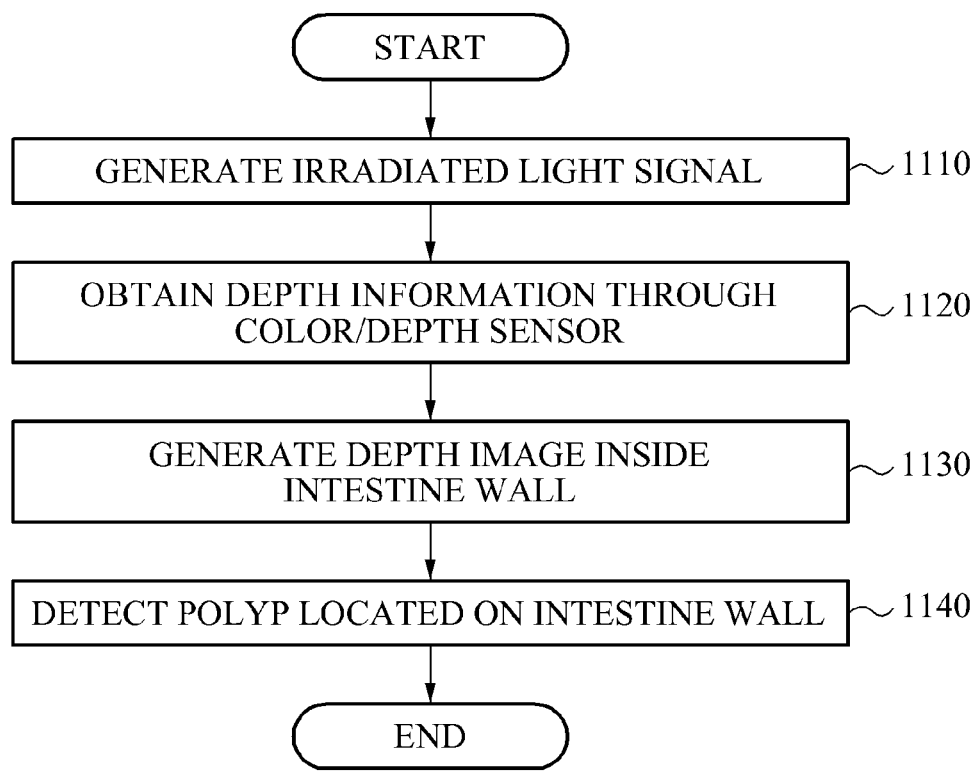
FIG. 11 illustrates a method for detecting a polyp by an endoscope using depth information according to example embodiments.

FIG. 11 illustrates a method for detecting a polyp by an endoscope using depth information according to example embodiments.

In operation 1110, the endoscope using the depth information may generate an irradiated light signal including a visible light from a light source. The endoscope using the depth information may generate an irradiated light signal including the visible light from the light source and an infrared ray. The endoscope using the depth information may generate an irradiated light signal including an infrared ray from the light signal.

In operation 1120, a color/depth sensor of the endoscope using the depth information may obtain depth information, based on a reflected light signal generated through the irradiated light signal being reflected off of an intestine wall. The color/depth sensor may obtain color information and depth information concurrently, based on an irradiated light signal and a reflected light signal.

The color/depth sensor may convert the reflected light signal to an electric signal for a pixel.

The color/depth sensor may use signals obtained through phase converting of the irradiated light signal as a control signal for operating a switch, and measure an electric charge accumulated by the electric signal in a capacitor connected to the switch, for a plurality of phases.

The color/depth sensor may calculate a phase and an average strength of the reflected light signal, based on the electric charge measured for the plurality of phases.

The color/depth sensor may determine the average strength of the reflected light signal calculated for the pixel to be color information for the pixel. The color/depth sensor may determine depth information for the pixel, based on a phase of the reflected light signal calculated for the pixel. The depth information may have a value proportional to a phase. The depth information may refer to a distance between the color/depth sensor and the intestine wall.

In operation 1130, the endoscope using the depth information may generate a depth image inside the intestine wall, based on the depth information obtained. The endoscope using the color information and the depth information may include an image processing unit that generates the depth image.

The endoscope using the depth information may model a form of an interior of the intestine wall, based on average depth information of the depth information obtained.

In operation 1140, the endoscope using the depth information may detect a polyp located on the intestine wall, based on the depth image.

According to example embodiments, the endoscope using the depth information may calculate a distance from a surgical tool disposed on a front portion of the endoscope to a polyp detected when the polyp is detected based on the depth information obtained from the color/depth sensor disposed on a side portion of the endoscope.

According to example embodiments, the endoscope using the depth information may down-sample the depth image inside the intestine wall in various scales.

According to example embodiments, the endoscope using the depth information may determine that the polyp is located at a position of a corresponding pixel when a depth value of a pixel in the depth image down-sampled is less than a depth value of neighboring pixels, by an amount differing from a threshold value.

According to example embodiments, the endoscope using the depth information may determine that the polyp is located at a position of a corresponding pixel when a matching error is greater than a threshold value when the depth information obtained and a form of the interior of the intestine wall are matched.

According to example embodiments, the endoscope using the depth information may obtain color information and depth information inside the intestine wall simultaneously, using the light source and the color/depth sensor disposed on the front portion and the side portion of the endoscope. The endoscope using the depth information may also generate a depth image, based on the depth information and automatically detect a position suspected of being a potential polyp, by comparing the depth information between the neighboring pixels in the depth image generated.

An additional light source may be unnecessary to obtain the depth information because the color information as well as the depth information may be obtained using the irradiated light signal modulated to a frequency of a visible light.

A polyp may be detected more precisely even when the front portion of the endoscope is restricted in rotating, by generating a form inside the intestine wall as a depth image, through obtaining the depth information from the color/depth sensor disposed on the side portion of the endoscope.

The method for detecting the polyp based on the endoscope using the depth information according to the above-described embodiments may be recorded in non-transitory computer-readable media including program instructions (computer readable instructions) to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although embodiments have been shown and described, it would be appreciated by those skilled in the art that changes may be made in these embodiments without departing from the principles and spirit of the disclosure, the scope of which is defined by the claims and their equivalents.

What is claimed is:

1. An endoscope using depth information, the endoscope comprising:
    a light source to generate an irradiated light signal including a visible light;
    a sensor to obtain depth information, based on the irradiated light signal and a reflected light signal generated by the irradiated light signal being reflected off of an intestine wall of an intestine, to convert the reflected light signal to an electrical signal, to use signals obtained from phase converting of the irradiated light signal as a control signal for operating a switch, to measure an electric charge accumulated by the electrical signal in a capacitor connected to the switch for a plurality of phases, and to calculate a phase and an average strength of the reflected light signal based on the electric charge measured for the plurality of phases; and
    an image processor to generate a depth image inside the intestine wall based on the depth information, and to detect a polyp located on the intestine wall based on the depth image.

2. The endoscope of claim 1, wherein the light source generates the irradiated light signal modulated to a frequency of the visible light while being disposed around the sensor.

3. The endoscope of claim 1, wherein the sensor obtains color information based on the irradiated light signal and the reflected light signal.

4. The endoscope of claim 1, wherein the sensor further comprises:
    a three-dimensional (3D) information determiner to determine depth information for a pixel based on the phase of the reflected light signal calculated for the pixel, and to determine the average strength of the reflected light signal calculated for the pixel to be color information for pixel.

5. The endoscope of claim 1, wherein the electric charge measurer uses four signals obtained from phase converting of the irradiated light signal in a unit of $\pi/2$ radians as the control signal for operating the switch, and measures the electric charge accumulated by the electrical signal in the capacitor connected to the switch, with respect to four phases.

6. The endoscope of claim 1, wherein the irradiated light signal further includes an infrared ray.

7. The endoscope of claim 1, wherein the light source and the sensor are disposed on at least one of a front portion of the endoscope initially entering the intestine and a side portion of the endoscope.

8. The endoscope of claim 7, further comprising:
a controller to calculate a distance from a surgical tool disposed on the front portion of the endoscope initially entering the intestine to a position of the detected polyp when the polyp is detected based on the depth information obtained from the sensor disposed on the side portion of the endoscope.

9. The endoscope of claim 1, wherein the image processor comprises:
a down-sampler to down-sample the depth image inside the intestine wall in various scales; and
a determiner to determine that the polyp is located at a position of a corresponding pixel when a depth value of a pixel in the down-sampled depth image is determined to be less than a depth value of neighboring pixels, by an amount differing from a threshold value.

10. The endoscope of claim 1, wherein the image processing unit comprises:
a modeler to model a shape of an interior of the intestine wall based on average depth information of the obtained depth information; and
a determiner to determine that the polyp is located at a position of a corresponding pixel when a matching error is greater than a threshold value through matching the obtained depth information and the modeled shape of the interior of the intestine wall for a pixel.

11. The endoscope of claim 1, wherein the light source generates a pulse of the irradiated light signal once per predetermined period.

12. The endoscope of claim 1, further comprising: a surgical tool disposed on a front portion of the endoscope initially entering an intestine.

13. The endoscope of claim 12, wherein the endoscope comprises:
a head portion on which the surgical tool is disposed; and
a supporting portion that bends in all directions while supporting the head portion.

14. The endoscope of claim 1, wherein the sensor calculates an electric charge stored in a pixel for the plurality of phases by convoluting the signals obtained through the phase converting and the reflected light signal.

15. An endoscope using depth information, the endoscope comprising:
a light source to generate an irradiated light signal including an infrared ray;
a sensor to obtain depth information, based on the irradiated light signal and a reflected light signal generated by the irradiated light signal being reflected off of an intestine wall of an intestine, to convert the reflected light signal to an electrical signal, to use signals obtained from phase converting of the irradiated light signal as a control signal for operating a switch, to measure an electric charge accumulated by the electrical signal in a capacitor connected to the switch for a plurality of phases, and to calculate a phase and an average strength of the reflected light signal based on the electric charge measured for the plurality of phases; and an image processor to generate a depth image inside the intestine wall based on the depth information, and to detect a polyp located on the intestine wall based on the depth image.

16. A method for detecting a polyp based on an endoscope using depth information, the method comprising:
generating an irradiated light signal including a visible light;
obtaining depth information, using a color/depth sensor, based on the irradiated light signal and a reflected light signal generated by the irradiated light signal being reflected off of an intestine wall of an intestine;
generating a depth image inside the intestine wall based on the depth information; and
detecting a polyp located on the intestine wall based on the depth image,
wherein the obtaining of the depth information comprises;
converting the reflected light signal to an electrical signal;
using signals obtained through phase converting of the irradiated light signal as a control signal for operating a switch;
measuring an electric charge accumulated by the electrical signal in a capacitor connected to the switch for a plurality of phases; and
calculating a phase and an average strength of the reflected light signal based on the electric charge measured for the plurality of phases.

17. The method of claim 16, wherein: the irradiated light signal further includes an infrared ray, and the method further comprises obtaining color information based on the irradiated light signal and the reflected light signal.

18. The method of claim 16, wherein the obtaining of the depth information further comprises:
determining depth information for a pixel based on a phase of the reflected light signal calculated for the pixel; and
determining an average strength of the reflected light signal calculated for the pixel to be color information for the pixel.

19. The method of claim 16, further comprising:
calculating a distance from a surgical tool disposed on a front portion of the endoscope initially entering the intestine to a position of the detected polyp when the polyp is detected based on the depth information obtained from the color/depth sensor disposed on a side portion of the endoscope.

20. The method of claim 16, wherein the detecting of the polyp comprises:
down-sampling the depth image inside the intestine wall in various scales; and
determining that the polyp is located at a position of a corresponding pixel when a depth value of a pixel in the down-sampled depth image is less than a depth value of neighboring pixels, by an amount differing from a threshold value.

21. The method of claim 16, wherein the generating of the depth image comprises:
modeling a shape of the interior of the intestine wall based on an average of the obtained depth information.

22. The method of claim 21, wherein the detecting of the polyp comprises:
determining that the polyp is located at a position of a corresponding pixel, when a matching error is greater than a threshold value, by matching the obtained depth information and the modeled shape of the interior of the intestine wall.

23. A computer program embodied on a non-transitory computer readable medium, the computer program being configured to control a processor to perform:
- generating an irradiated light signal including a visible light;
- obtaining depth information, using a color/depth sensor, based on the irradiated light signal and a reflected light signal generated by the irradiated light signal being reflected off of an intestine wall of an intestine;
- generating a depth image inside the intestine wall based on the depth information; and
- detecting a polyp located on the intestine wall based on the depth image,
- wherein the obtaining of the depth information comprises;
- converting the reflected light signal to an electrical signal;
- using signals obtained through phase converting of the irradiated light signal as a control signal for operating a switch;
- measuring an electric charge accumulated by the electrical signal in a capacitor connected to the switch for a plurality of phases; and
- calculating a phase and an average strength of the reflected light signal based on the electric charge measured for the plurality of phases.

* * * * *